United States Patent
Rivas Alvarez (10) Patent No.: US 8,604,923 B1
(45) Date of Patent: Dec. 10, 2013

(54) TELEMETRIC HEALTH MONITORING DEVICES AND SYSTEM

(76) Inventor: Victor Rivas Alvarez, Lincoln, NE (US)

( * ) Notice: Subject to any disclaimer, the term of this patent is extended or adjusted under 35 U.S.C. 154(b) by 1082 days.

(21) Appl. No.: 12/460,306

(22) Filed: Jul. 16, 2009

Related U.S. Application Data (60) Provisional application No. 61/135,071, filed on Jul. 16, 2008.

(51) Int. Cl.
*G08B 1/08* (2006.01)
(52) U.S. Cl.
USPC ............. 340/539.12; 340/573.1; 600/300
(58) Field of Classification Search
USPC ............. 340/573.1, 539.11, 539.12, 870.16; 600/300, 301
See application file for complete search history.

(56) References Cited

U.S. PATENT DOCUMENTS

| | | | |
|---|---|---|---|
| 5,294,831 A | 3/1994 | Azar et al. | |
| 6,160,478 A * | 12/2000 | Jacobsen et al. | 340/539.12 |
| 6,416,471 B1 * | 7/2002 | Kumar et al. | 600/300 |
| 6,621,040 B1 | 9/2003 | Perry et al. | |
| 6,627,844 B2 | 9/2003 | Liu et al. | |
| 6,738,671 B2 * | 5/2004 | Christophersom et al. | 128/903 |
| 6,800,828 B2 | 10/2004 | Golecki | |
| 6,907,921 B2 | 6/2005 | Insley et al. | |
| 7,009,511 B2 * | 3/2006 | Mazar et al. | 340/531 |
| 7,262,487 B2 | 8/2007 | Farnworth et al. | |
| 7,376,238 B1 | 5/2008 | Rivas et al. | |
| 7,386,121 B1 | 6/2008 | Rivas | |
| 7,400,257 B2 | 7/2008 | Rivas | |
| 7,440,280 B2 | 10/2008 | Shuy | |
| 7,545,640 B2 | 6/2009 | Fisher et al. | |
| 7,651,253 B2 | 1/2010 | Shuy | |
| 2004/0130446 A1 * | 7/2004 | Chen et al. | 340/539.12 |
| 2004/0188066 A1 | 9/2004 | Upadhya et al. | |
| 2005/0263269 A1 | 12/2005 | Kaneko et al. | |
| 2006/0066449 A1 * | 3/2006 | Johnson | 340/539.12 |
| 2006/0102601 A1 | 5/2006 | Shirk et al. | |
| 2006/0157234 A1 | 7/2006 | Golecki | |
| 2007/0046476 A1 * | 3/2007 | Hinkamp | 340/573.1 |
| 2008/0030346 A1 * | 2/2008 | Despotis | 340/573.1 |
| 2008/0216926 A1 | 9/2008 | Guo et al. | |
| 2008/0299408 A1 | 12/2008 | Guo et al. | |
| 2010/0099268 A1 | 4/2010 | Timans | |
| 2010/0219506 A1 | 9/2010 | Gupta et al. | |

* cited by examiner

*Primary Examiner* — Thomas Mullen
(74) *Attorney, Agent, or Firm* — James Creighton Wray

(57) ABSTRACT

A wrist watch receives local measurements and remote instructions and provides reports of measurements to remote processors for review by physicians. Chest straps, pressure cuffs and onboard sensors provide information. The wrist watch, chest strap and cuff are inductively charged. Wrist watches, straps, cuffs, sensors and chargers are distributed with no or low costs to encourage use. Patient's health and public health are assessed economically without time and cost consuming travel and office visits.

13 Claims, 10 Drawing Sheets

TELEMETRIC HEALTH MONITORING DEVICES AND SYSTEM

This application claims the benefit of U.S. Provisional Application No. 61/135,071, filed Jul. 16, 2008, which is hereby incorporated by reference in its entirety.

SUMMARY OF THE INVENTION

The invention provides a new telemetric watch and chest band system for providing data over radio waves via an antenna to processing centers which process the data and send information to a system.

The physician sends instructions and requests to the processing center which encodes and sends the instructions and requests via antennas to a patient's watch, where they are displayed.

The telemetric watch will send raw data at a pre-set sampling rate to a radio tower. The radio tower passes raw data to data processing center. Data is processed. The physician receives the processed data via the Internet.

The physician sends a message via the Internet to processing center. The processing center receives messages from the physician and transmits them to the radio tower. The radio tower transmits data to a user's watch. The watch receives data and displays it to the patient, for example, requesting a blood pressure reading.

In the example, the patient uses a wireless blood pressure cuff which transmits data to the watch. The raw data is forwarded from the watch to the radio tower. The radio tower transmits data to the processing center. Data is processed and provided to the physician.

Messages may communicate alerts to take medication, call a physician for medical direction or appointments or provide any direct message from the physician to the patient.

A telemetric chest strap will send raw data at a pre-set sampling rate via Bluetooth to the telemetric watch. The watch will send the raw data at a pre-set sampling rate to the radio tower.

The radio tower passes the raw data to the data processing center. Data is processed, and the physician receives data via the internet.

Other telemetric devices can be used in the system besides watches and chest straps. For example, a telemetric bracelet or ring or telemetric sunglasses can serve the same purposes as the telemetric watch, monitoring blood pressure, heart rate, and temperature and sending the data via Bluetooth or another wireless signal to another device. This other device may be a PDA or mobile phone, such as the mobile phone described in U.S. Pat. No. 7,386,121, which is hereby incorporated by reference in its entirety. Typically these non-watch devices would use a mobile phone or another similar device (such as PDA) as a display. More details on pulse rate, blood pressure, and heart condition monitoring glasses can be found in U.S. Pat. Nos. 7,376,238 and 7,400,257, which are hereby incorporated by reference in their entirety.

A telemetric implant can also be used. An implant, in addition to measuring blood pressure, heart rate, and temperature, can also monitor the levels of various indicators in the blood stream, including glucose, micronuclei, cholesterol, and oxygen levels.

Each of the telemetric devices can deliver data to a mobile phone. The mobile phone can give a distinct ringtone alert if vital signs are out of trend. The data can be displayed on the mobile phone and the phone can also save the data for later review and/or send the data on to another device or mobile phone. The phone can give the user an option to send data to a doctor or caregiver, or can do so automatically.

These and other objects and features of the invention are apparent in the disclosure, which includes the above and ongoing written specification, with the claims and drawings.

DETAILED DESCRIPTION

Figure 1:
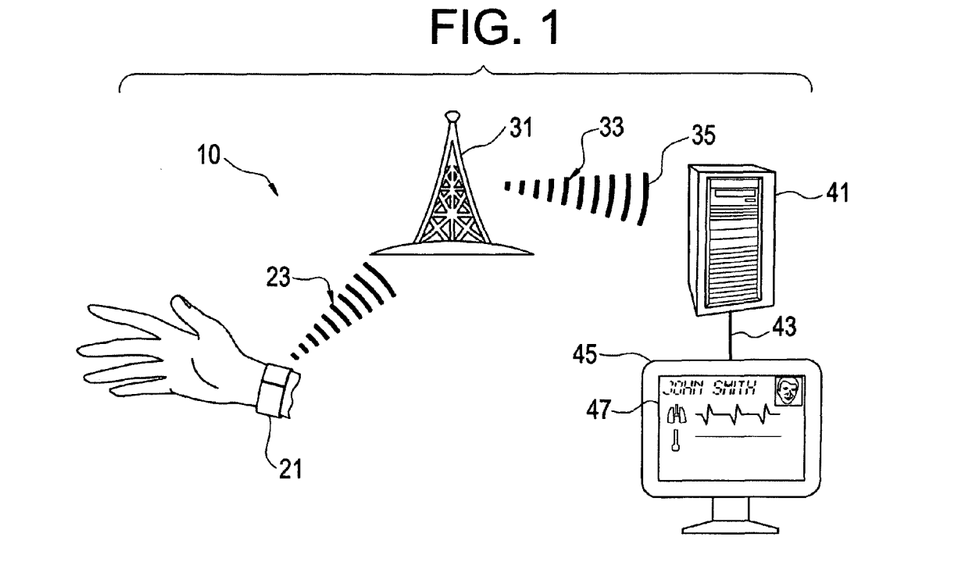
FIG. 1 shows a telemetric watch sending information to a physician.

As shown in FIG. 1 in a telemetric watch system 10, a telemetric wrist watch 21 sends 23 raw data at a preset sampling rate to a radio tower 31. Radio tower 31 passes 33 the raw data to a receiver in a data processing center 41 by radio waves 35 or ground lines. The raw data is processed by the data processing center and transmitted 43 via the Internet, to a physician's work station 45. Identifying patient information and physical patient metrics are displayed on the screen 47 at the work station 45.

Figure 2:
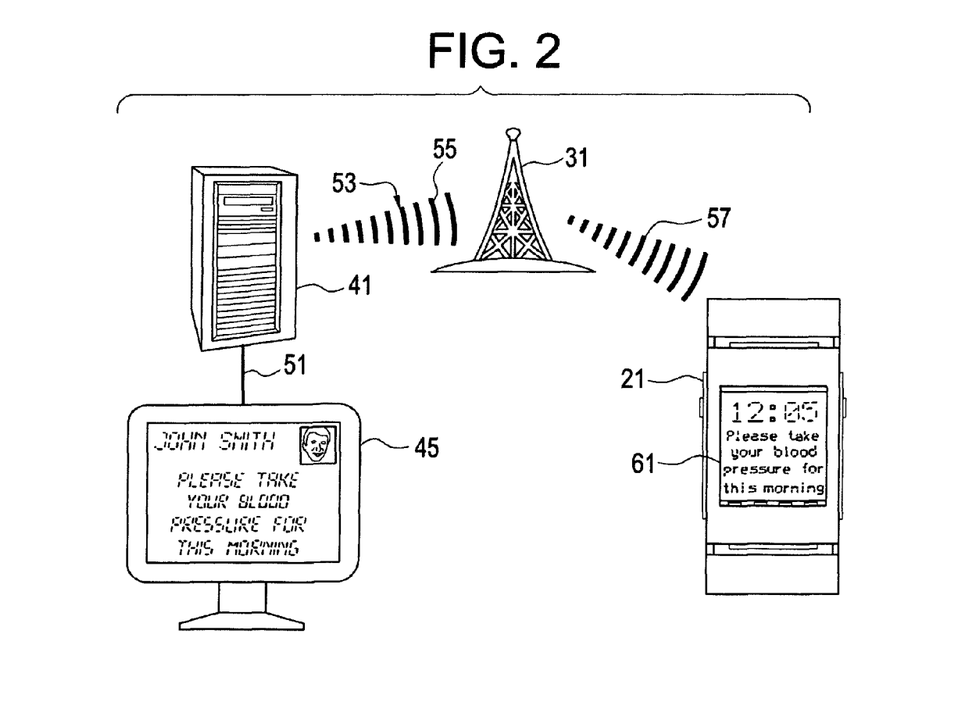
FIG. 2 shows the physician sending instructions to the patient's watch.

As shown in FIG. 2, the physician sends 51 messages from her work station 45 via the Internet to data processing center 41, which sends 53 the information by land lines or radio waves 55 to radio tower 31, which repeats the information and sends 57 the information to the patient's watch 21. A display 61 on the watch 21 displays the message from the physician to the patient, in this example requesting a blood pressure reading.

Figure 3:
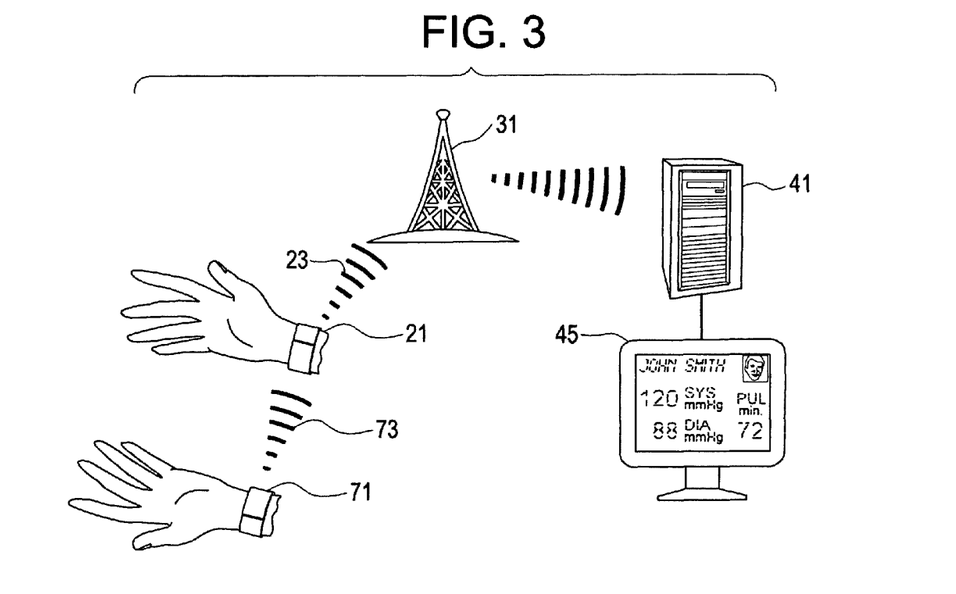
FIG. 3 shows a patient sending the requested data.

As shown in FIG. 3, the patient uses a wireless blood pressure cuff 71 which transmits 73 data to watch 21. The raw data is sent 23 via the radio tower 31 and the data processing center 41 to the physician's workstation 45, where the patient's identification, photograph and requested blood pressure is shown on the display 47.

Figure 4:
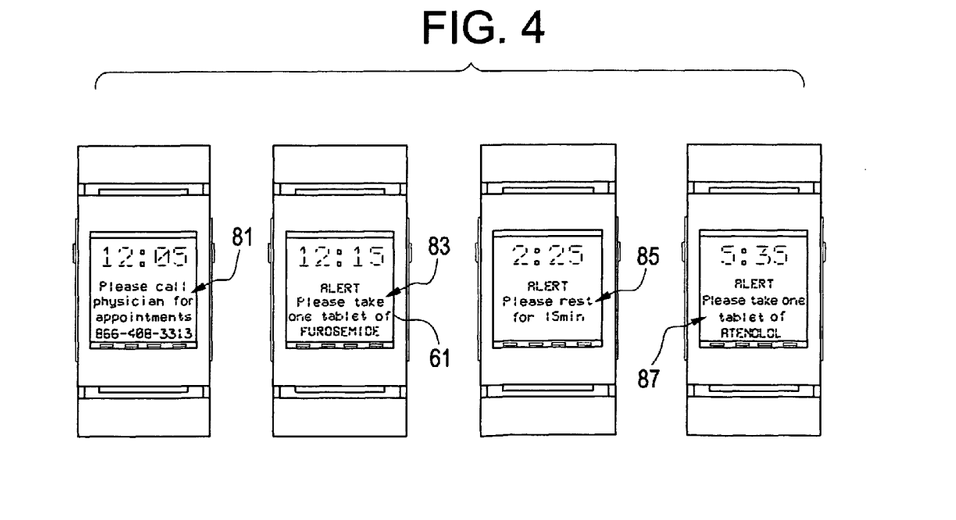
FIG. 4 shows messages sent to a patient's watch from a physician.

FIG. 4 shows several messages 81, 83, 85, 87 which can be automatically transmitted to the patient's watch 21 and shown on the watch display 61, wherein the display of the wrist watch 21 may be a conventional digital or analog timepiece.

Figures 5, 6, 7:
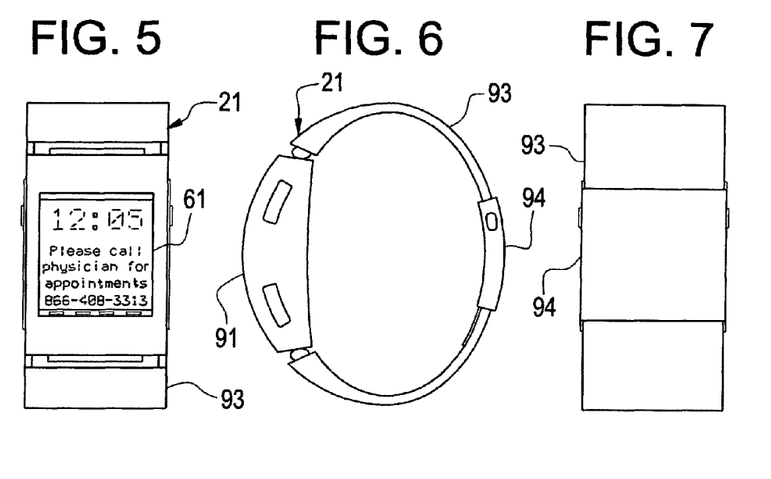
FIGS. 5-7 show details of the telemetric watch.

FIGS. 5, 6 and 7 show front, side and rear elevations of a patient's watch 21 showing the computer and transmitter 91 supported by band 93 and clasp 94.

Figure 8:
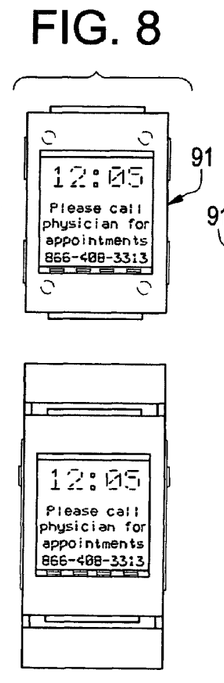
FIGS. 8-10 show details of the sensor, computer and communicator on the telemetric watch.
Figure 9:
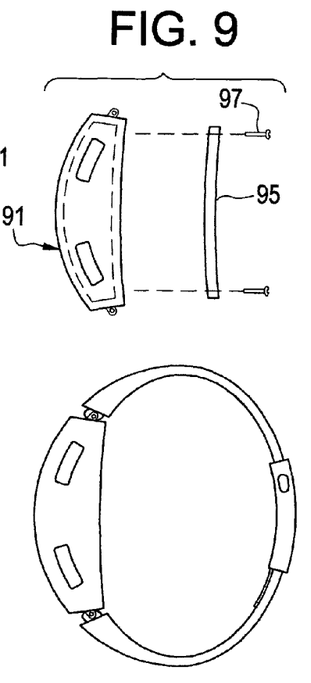
Figure 10:
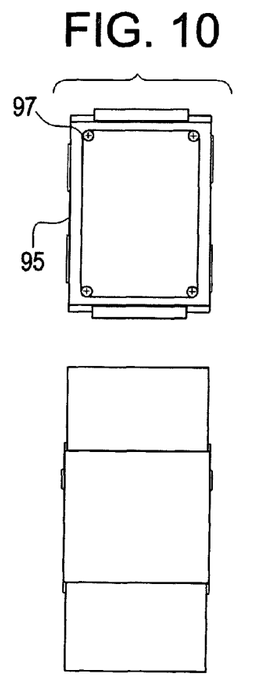

FIGS. 8, 9 and 10 show mounting of the computer and transmitter 91 with a sensor plate 95 and screws 97.

Figure 11:
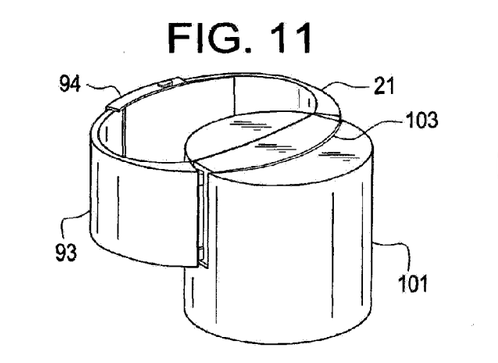
FIG. 11 shows a charger for the sensor, computer and communicator on the telemetric watch.
Figure 12:
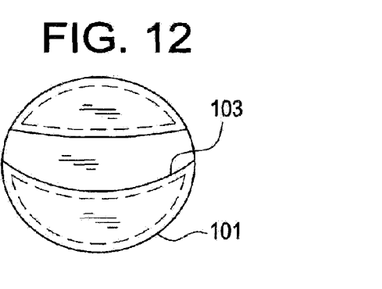
FIGS. 12-16 show details of the charger.
Figure 13:
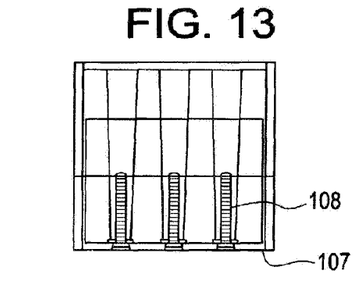
Figure 14:
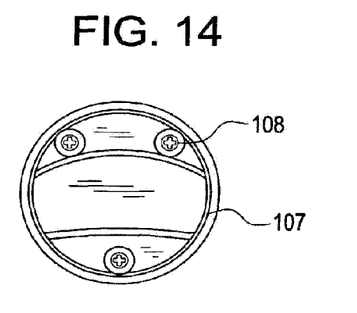
Figure 15:
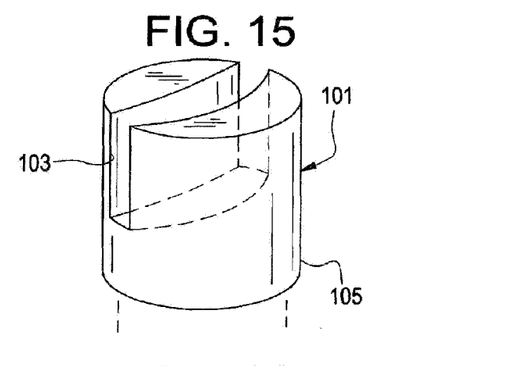
Figure 16:
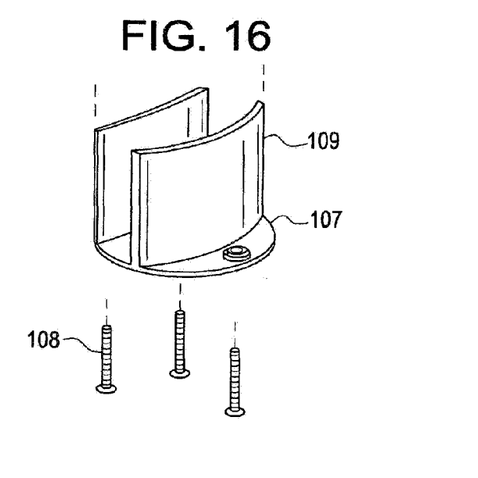

FIG. 11 shows a charger 101 with a slot 103 which fits over the computer and transmitter 91 to charge a capacitor or battery with the patient's watch 21.

FIG. 12-16 show features of the charger 101 with the curved slot 103. The charger has a cover 105 and a base 107 which is secured to the cover with screws 108. The base 107 has upstanding spaced electromagnetic cores 109 which are used in a contact-less charging of the computer and transmitter 91 on the wrist watch 21.

A telemetric chest strap system 110 is shown in FIGS. 17-25.

Figure 17:
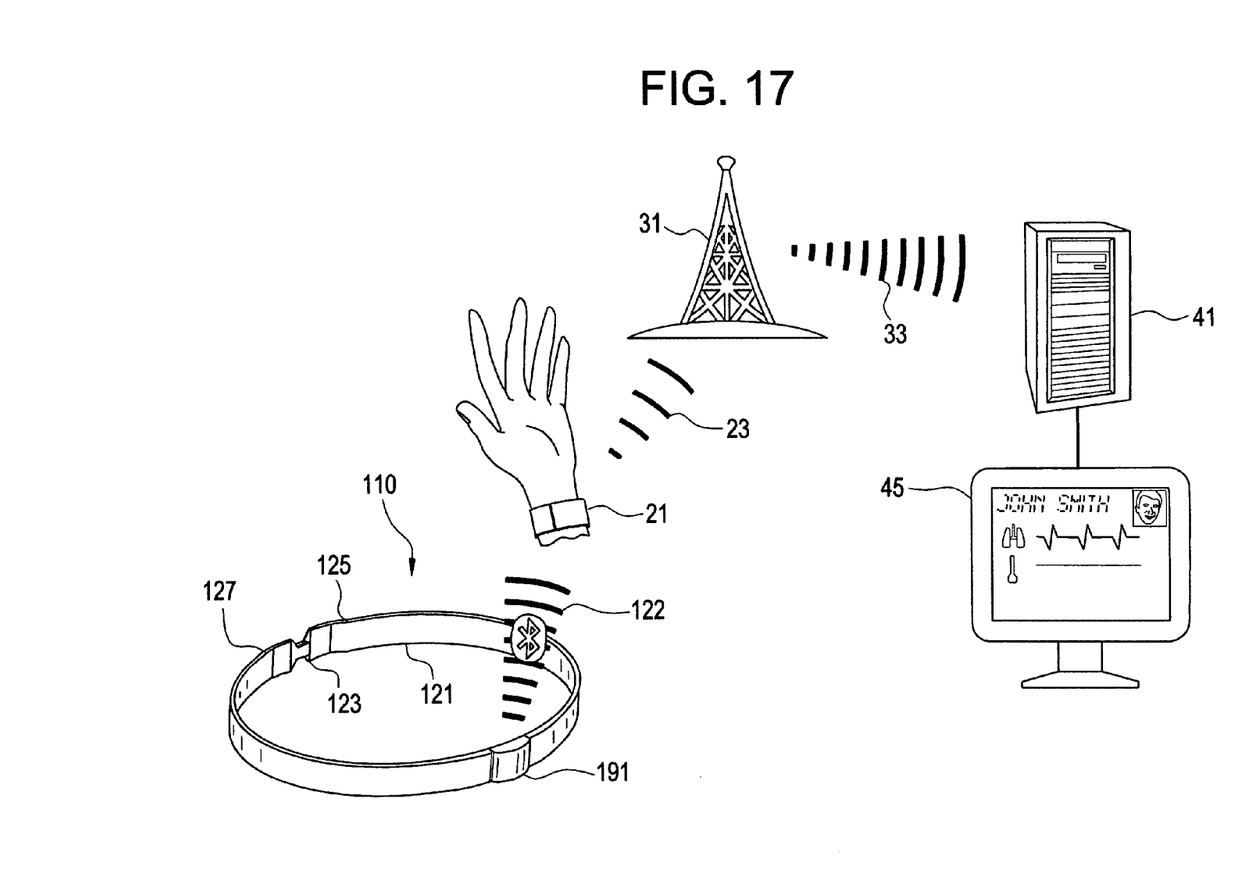
FIG. 17 shows a telemetric chest strap.

The chest strap 121 sends 122 raw data by localized Bluetooth communication to the telemetric watch 21. In a telemetric watch system 10, a telemetric wrist watch 21 sends 23 raw data received from the chest strap 121 at a preset sampling rate to a radio tower 31. Radio tower 31 passes 33 the raw data to a receiver at data processing center 41 by radio waves 35 or ground lines. The raw data is processed by the data processing center and transmitted 43 via the Internet, to a physician's work station 45. Identifying patient information and physical patient metrics are displayed on the screen 47 at the work station 45.

Figures 18, 19:
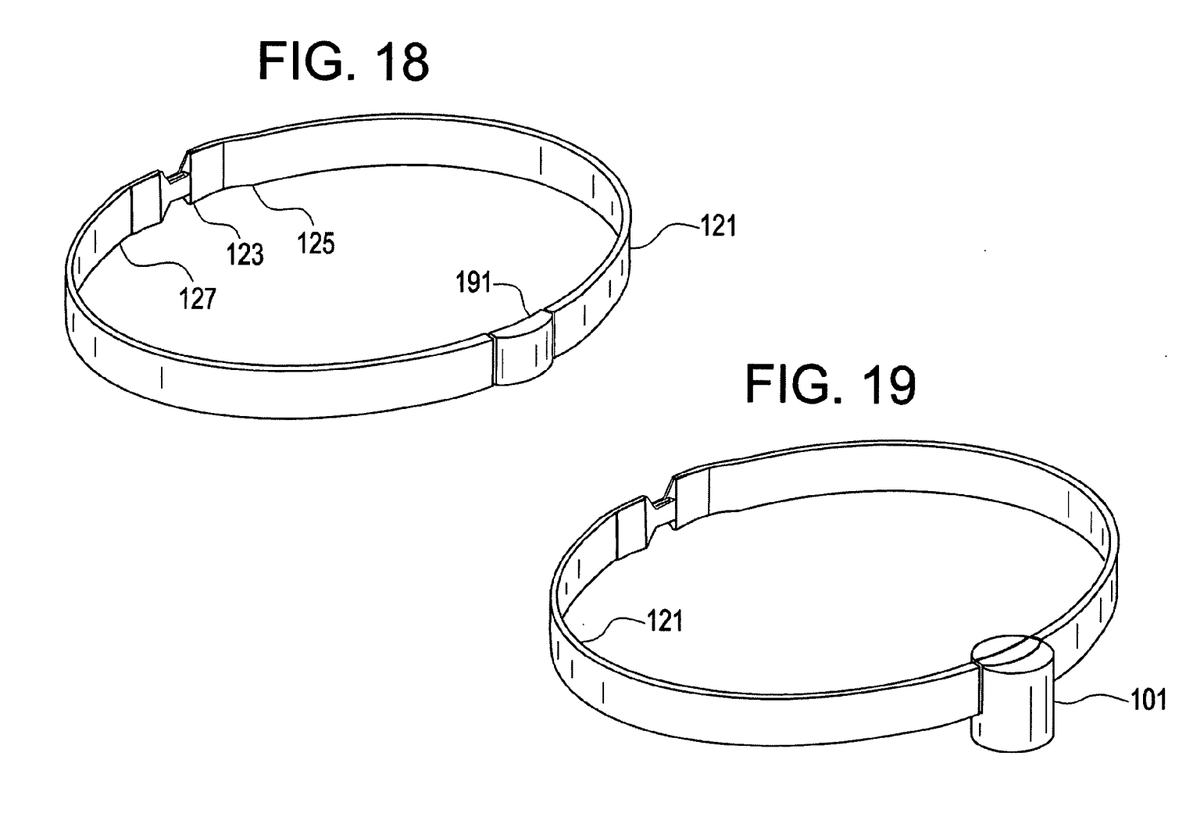
FIG. 18 shows elements of the telemetric chest strap.
FIG. 19 shows a charger on the telemetric chest strap.
Figures 20, 21, 22, 23, 24, 25:
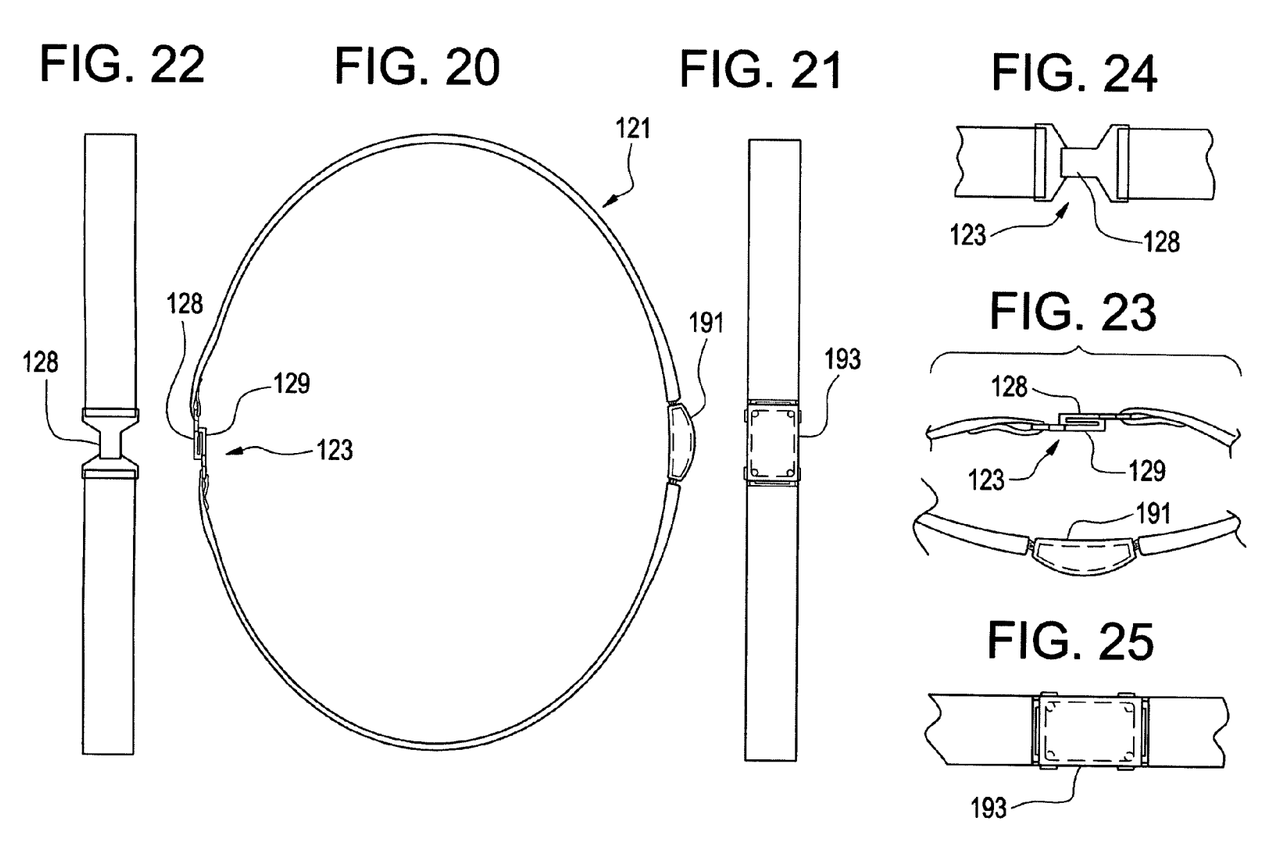
FIGS. 20-25 shows details of the telemetric chest strap.

The chest strap 121 as shown in FIGS. 18 and 19 has a sensor-computer-transmitter 191 similar to computer-transmitter 91 on the wrist watch 21. A clasp 123 holds ends 125, 127 of the chest strap together. A module 191 is similar to module 91 on the wrist watch 21. Charger 101 is the same charger used with wrist watch 21.

Parts 128, 129 of clasp 123 are shown in FIGS. 20, 22, 23 and 24. The insert sensor plate 193 on module 191 is shown in FIGS. 21 and 25.

Figure 26:
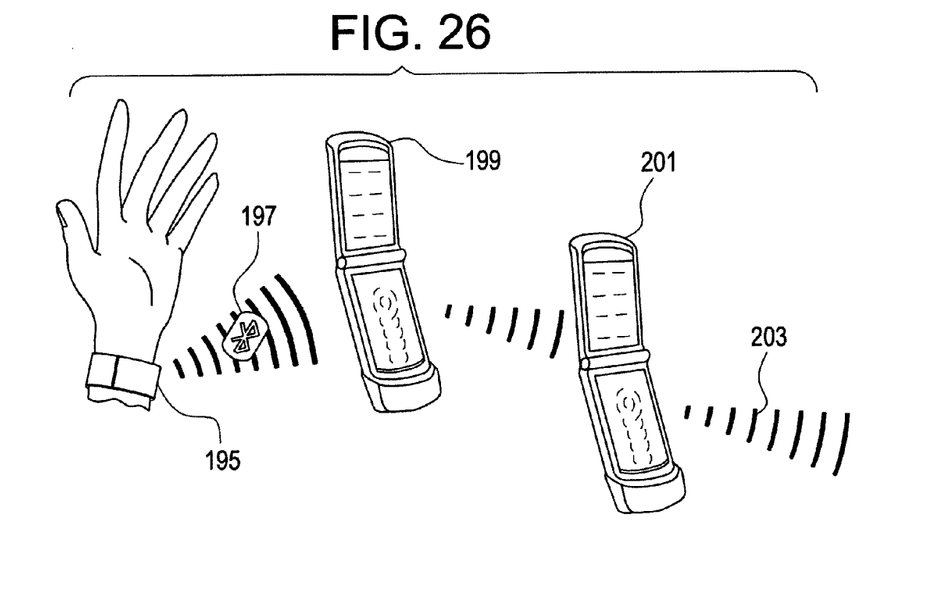
FIG. 26 shows a telemetric bracelet sending data to a mobile phone, which is forwarding this data to another mobile phone, which is sending this data onward.

FIG. 26 shows a telemetric bracelet 195 that monitors blood pressure, heart rate, and temperature and sends raw data 197 at a pre-set sampling rate to a Bluetooth-enabled cell phone 199. This cell phone 199 sends raw data via a phone call to another mobile phone 201. This second cell phone may be the phone of a caretaker, such as a family member or friend. This second phone 201 can then send the data 203 to a physician via his cell phone or to another person.

Figure 27:
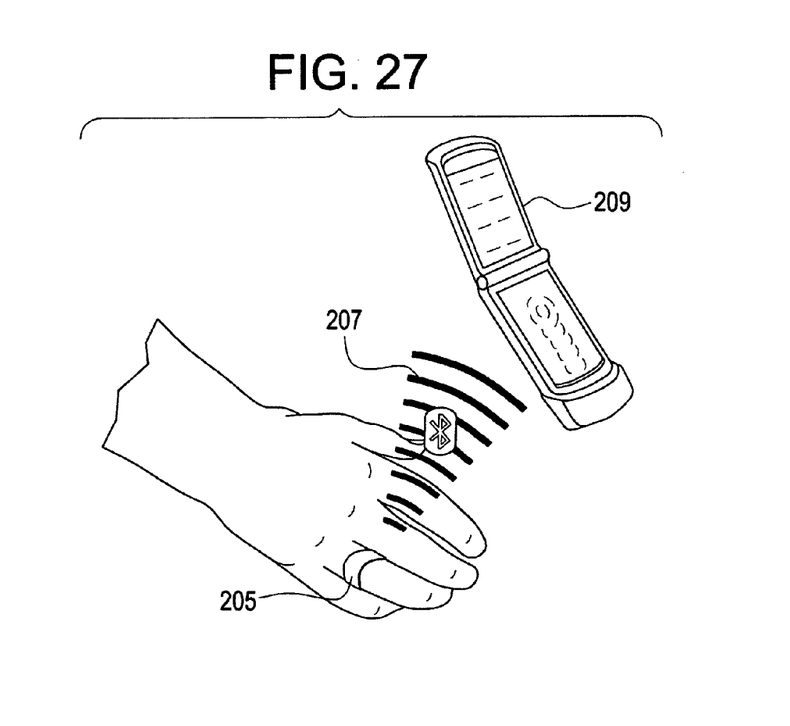
FIG. 27 shows a telemetric ring sending data to a mobile phone.
Figure 28:
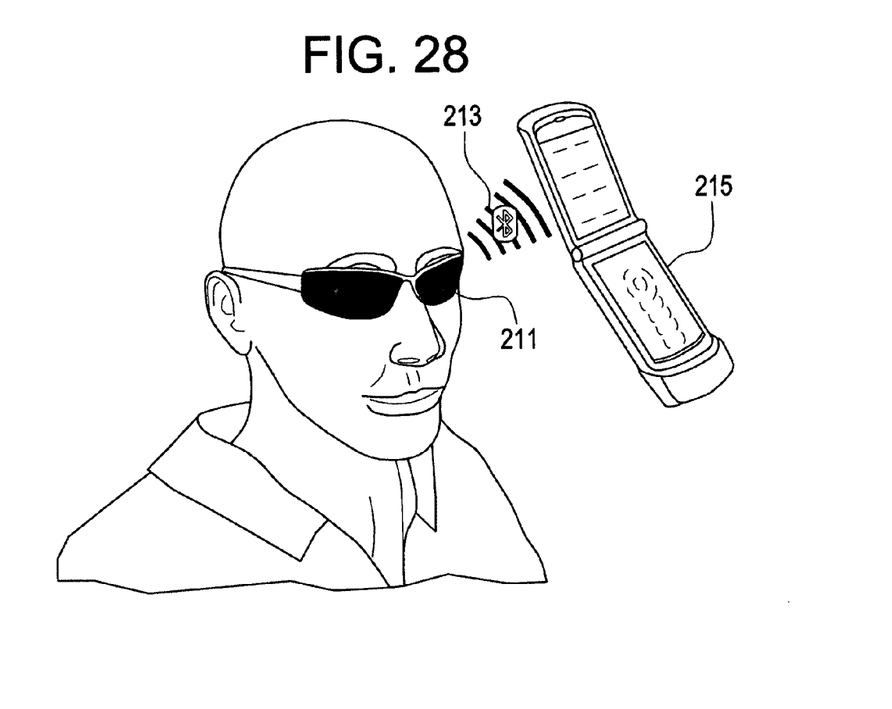
FIG. 28 shows telemetric glasses sending data to a mobile phone.

FIG. 27 shows a telemetric ring 205 for measuring blood pressure, heart rate, and temperature and sending data 207 via Bluetooth to a mobile phone 209. FIG. 28 shows telemetric glasses 211 for measuring blood pressure, heart rate, and temperature and sending data 213 via Bluetooth to a mobile phone 215.

Once data has been delivered to a mobile phone, the phone can give a distinct ringtone alert if vital signs are out of trend. The data can be displayed on the mobile phone and the phone can also save the data for later review and/or send the data on to another device or mobile phone. The phone can give the user an option to send data to a doctor or caregiver, or can do so automatically.

Figure 29:
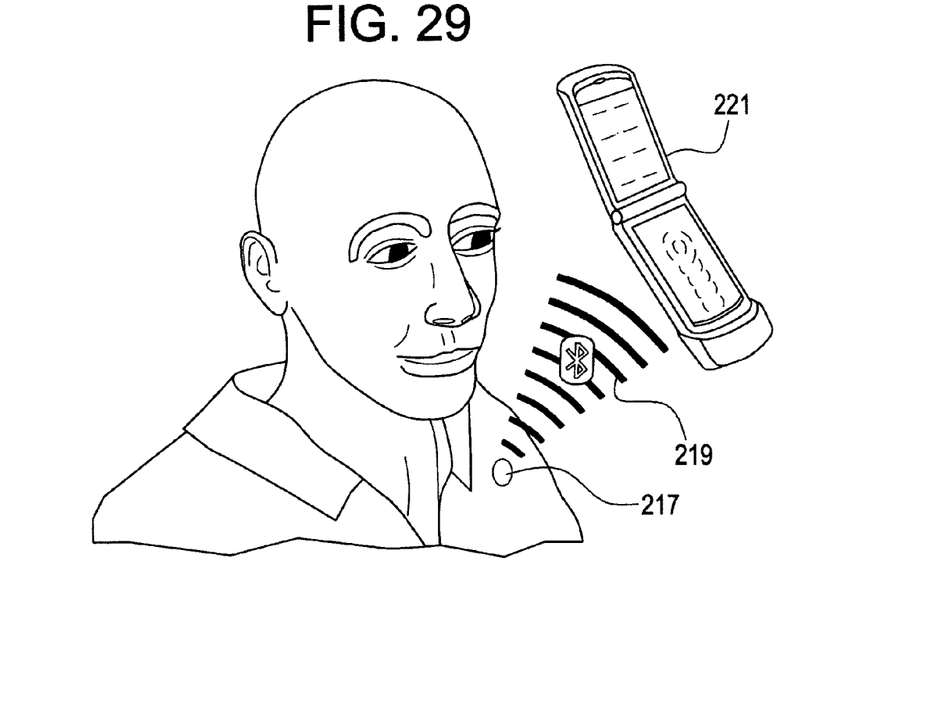
FIG. 29 shows a telemetric implant sending data to a mobile phone.

FIG. 29 shows a telemetric implant 217 that, in addition to measuring blood pressure, heart rate, and temperature, can also measure the level of various indicators in the bloodstream, such as glucose, oxygen, micronuclei, and cholesterol levels, and send this data 219 via Bluetooth to a mobile phone 221. Monitoring of oxygen level in the bloodstream (oximetry) can be useful, for example, for various medical conditions affecting the heart and lungs, for determining the effectiveness of or need for supplemental oxygen, and for pilots in unpressurized aircraft. An implant near a healing wound can use oxygen levels to predict the onset of gangrene. Continuous monitoring of glucose levels is very important for diabetics, cholesterol is an indicator of heart disease, and micronuclei levels in the bloodstream are an indicator of cancer risk.

Figure 30:
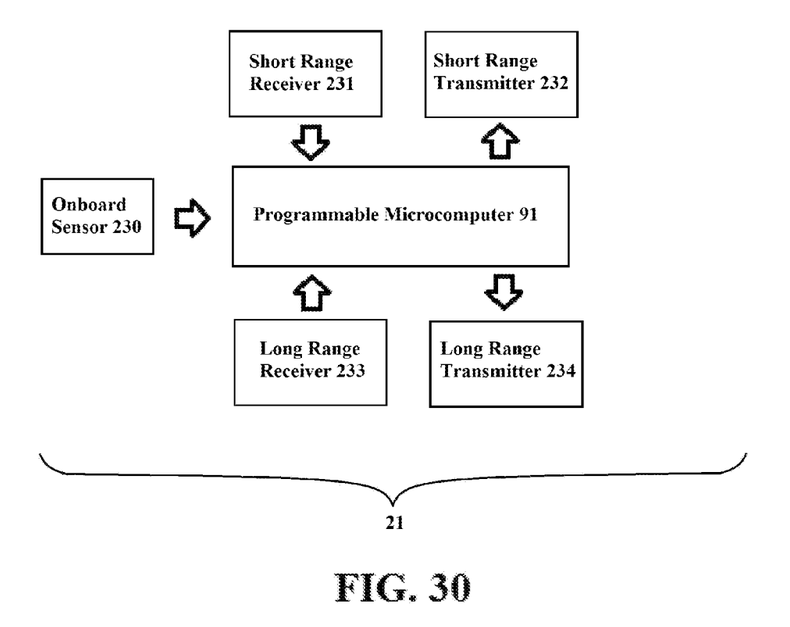
FIG. 30 shows a block diagram of the telemetric watch 21.

FIG. 30 shows a block diagram of the telemetric wrist watch 21, wherein the wrist watch has an onboard sensor 230, a short range receiver 231, a long range receiver 233, a long range transmitter 234, a short range transmitter 232, and a programmable microcomputer 91.

Tumors and cancers are the result of genetic damage, which often includes the formation of micronuclei. The presence of micronuclei in living cells indicates that the cells can no longer properly repair broken DNA. This deficiency heightens the risk of developing cancer. Micronuclei in human blood cells are a type of genetic damage known to be a diagnostic marker for cancer. Measurements of micronuclei levels in the blood cells of children were used in the aftermath of Chernobyl to identify those children most at risk of developing cancer and to begin preventative treatments.

These measurements are therefore of interest to the population as a whole, but particularly to those who have suffered from cancer in the past and are at risk for recurrence. Continuous monitoring of micronuclei is a boon to such patients, who in the past needed to weigh the burden of constant trips to a doctor's office against the risks of developing cancer between visits.

A wrist band which may be a bracelet or watch band contains an identification code and senses vital signs of a wearer and automatically reports out-of-range vital sign indications to a remote health center.

The wrist band contains a pulse rate sensor, a blood pressure sensor, a temperature sensor, a power source, a timer, a memory, a comparator, an encoder and a low power radio frequency transmitter. The wrist band also includes a watch as an incentive for a user to wear the wrist band.

The encoder digitally encodes the user identification.

The wrist band includes a receiver for remote queries of information or data from specific wrist bands. The memory is programmable on the wrist band or remotely to adjust in-range limits or to vary periodic sensing intervals according to known health conditions of the wearer.

Periodically, the wrist band mounted sensors sense, whether sequentially or concurrently, heart rate (pulse rate), blood pressure and temperature. The sensed results and their predetermined acceptable ranges stored in the memory are compared for out-of-range perturbations. The out-of-range perturbations are stored in the memory digitally encoded by the encoder and, with the encoded user identification, are transmitted by the transmitter.

The transmissions are received by towers in range of the transmitters and are relayed to central processors. The central processors retransmit the data to a local health center that has cognizance of the health of the identified individual user.

The sensor, comparator, encoder and transmitter sequence may be activated by buttons on the wrist band by a user who feels a physical event or by a person giving aid to a user.

The wrist bands and watches initially are distributed to ambulatory out-patients who are found to be in need of monitoring after examination in local health centers. Subsequently, the wrist bands, bracelets and watches are distributed to other groups such as workers in hazardous environments, public safety officers, government employees and others.

In areas, political divisions or countries in which citizens have permanently assigned numerical identifications, those digitized identifications may be permanently stored in the wrist band memory.

While the invention has been described with reference to specific embodiments, modifications and variations of the invention may be constructed without departing from the scope of the invention, which is defined in the following claims.

I claim:

1. A first telemetric wrist-worn accessory comprising a strap and a wrist watch, wherein the wrist watch has an onboard sensor, a short range receiver, a long range receiver, a long range transmitter, a short range transmitter and a programmable microcomputer,
wherein the strap holds the wrist watch, sensor, receivers, transmitters and microcomputer on a wrist of a single user,
wherein the wrist watch is a conventional digital or analog time piece,
wherein the short range receiver receives low power short range signals from transmitters of a second telemetric sensor device nearby, wherein the second device is worn separately by the single user,
wherein the long range receiver receives radio wave signals from a remote processor via communication towers,
wherein the long range transmitter transmits radio wave signals to the remote processor via the communication towers,
wherein the short range transmitter transmits low power inquiry signals to receivers of the second telemetric sensor device,
wherein the short range transmitter is controlled by the programmable microcomputer to transmit the low power inquiry signals to receivers of the second telemetric device as a request for data from nearby sensors of the second telemetric sensor device, and wherein the programmable microcomputer extracts and stores data from the onboard sensor and from the low power short range signals from the nearby sensors via the transmitters of the second telemetric device, and
wherein the long range radio transmitter is controlled by the programmable microcomputer to transmit long range radio wave signals comprising the extracted data to the remote processor via the communication towers.

2. A health monitoring method comprising:
distributing first telemetric wrist watches, the wrist watches each having one or more receivers, transmitters, microcomputers and sensors; wherein for each wrist watch,
registering coordinated identification of a wrist watch worn on a single user with user identification of the single user,
providing instructions from a medical office via a processor and transmission towers to the wrist watch, wherein the instructions request reading of nearby sensors in a second telemetric sensor device, wherein the second device is worn separately by the user,
processing the request in the microcomputer on the wrist watch,
sending short range inquiry signals to the nearby sensors in the second telemetric sensor device,
receiving data signals in the wrist watch from the nearby sensors in the second telemetric sensor device,
extracting data from the received data signals,
storing the extracted data from the received data signals in a memory connected to the one or more microcomputers, and
transmitting radio wave signals containing the extracted data from the memory and the wrist watch identification to the medical office via the transmission towers and the processor.

3. The method of claim 2, further comprising:
periodically sending the short range inquiry signals to the nearby sensors of the second telemetric sensor device and sending the data signals from the nearby sensors, and receiving, extracting and storing the data from the data signals in the memory connected to the one or more microcomputers,
periodically transmitting the extracted data from the memory and the wrist watch identification to the processor, and storing the data in memory connected to the processor.

4. The method of claim 3, further comprising:
periodically sending the extracted data from the memory connected to the processor to the medical office for review and study.

5. The method of claim 3, further comprising:
comparing the extracted data from the memory connected to the processor with in-range vital sign data, and reporting out-of-range data to the medical office.

6. The method of claim 2, further comprising:
comparing the extracted data stored in the memory connected to the microcomputers with in-range vital sign data, and reporting out-of-range data to the medical office via the transmission towers and the processor.

7. A health monitoring method comprising:
distributing first telemetric wrist watches, the wrist watches each having one or more receivers, transmitters, microcomputers and sensors; wherein for each wrist watch,
registering user identification of a wrist watch with a single user, wherein the wrist watch is worn on the user,
controlling via the one or more microcomputers a short range transmitter to transmit low power inquiry signals to nearby sensors in a second telemetric sensor device, wherein the second telemetric sensor device is worn separately on the user,
receiving data signals in the wrist watch from the nearby sensors in the second telemetric sensor device,
extracting data from the received data signals with the one or more microcomputers,
storing the extracted data from the received data signals in memory connected to the one or more microcomputers, and
transmitting radio wave signals containing the extracted data from the memory and the wrist watch identification to transmission towers and a processor.

8. The method of claim 7, further comprising:
periodically sending the inquiry signals to the nearby sensors of the second telemetric sensor device, and sending the data signals from the nearby sensors and receiving, extracting and storing the data from the data signals in the memory connected to the one or more microcomputers,
periodically transmitting the extracted data from the memory and the wrist watch identification to the processor via the transmission towers, and storing the data in memory connected to the processor.

9. The method of claim 8, further comprising:
periodically sending the extracted data from the memory connected to the processor to a medical office for review and study.

10. The method of claim 8, further comprising:
comparing the extracted data from the memory connected to the processor with in-range vital sign data, and reporting out-of-range data to a medical office.

11. The method of claim 7, further comprising:
comparing the extracted data stored in the memory connected to the one or more microcomputers with in-range vital sign data, and reporting out-of-range data to the processor via the transmission towers.

12. The health monitoring method of claim 7, wherein the second telemetric sensor device is a body-attachable device which comprises one or more of a chest strap and a cuff, the or each body-attachable device having one or more sensors and a transmitter in communication with the same wrist watch of the same single user.

13. The health monitoring method of claim 12, further comprising inputting inductive charges for charging power supplies of the watch, the chest strap and the cuff.

\* \* \* \* \*